United States Patent [19]
Beck

[11] Patent Number: 4,649,931
[45] Date of Patent: Mar. 17, 1987

[54] SAMPLED DATA SENSE AMPLIFIER

[75] Inventor: Robert C. Beck, St. Paul, Minn.

[73] Assignee: Medtronic, Inc., Minneapolis, Minn.

[21] Appl. No.: 239,807

[22] Filed: Mar. 2, 1981

[51] Int. Cl.$^4$ .............................................. A61B 5/04
[52] U.S. Cl. ............................ 128/708; 128/419 PG; 128/902
[58] Field of Search ............... 128/696, 689, 702, 703, 128/704, 706, 708, 902, 419 PG

[56] References Cited

U.S. PATENT DOCUMENTS

| | | | |
|---|---|---|---|
| 3,606,882 | 9/1971 | Abe et al. | 128/704 |
| 3,654,916 | 4/1972 | Neilson | 128/702 |
| 3,908,640 | 9/1975 | Page | 128/689 |
| 4,023,564 | 5/1977 | Valiquette et al. | 128/704 |
| 4,059,116 | 11/1977 | Adams | 128/419 PG |

OTHER PUBLICATIONS

Yannis P. Tsividis, "Analysis of Switched Capacitive Networks", *IEEE Transactions on Circuits and Systems*, vol. CAS-26, No. 11, Nov. 1979.
"ICL7600/ICL7601 Commutating Auto-Zero (CAZ) Operational Amplifier", *Intersil*, Intersil, Inc., Calif., 1979, pp. 1-6.
Ken Martin, "Improved Circuits for the Realization of Switched-Capacitor Filters", *IEEE Transactions on Circuits and Systems*, vol. CAS-27, No. 4, Apr. 1980.

*Primary Examiner*—William E. Kamm
*Attorney, Agent, or Firm*—Robert C. Beck; Joseph F. Breimayer; John L. Rooney

[57] ABSTRACT

A sense amplifier for a cardiac pacemaker which has an amplifier section with two feedback paths. One path contains small valued capacitors and clock activated switches to form a discrete time feedback path. The other path contains unclocked passive components to form a continuous time feedback path. The sense amplifier generates a detect signal in response to a depolarization of cardiac tissue.

2 Claims, 3 Drawing Figures

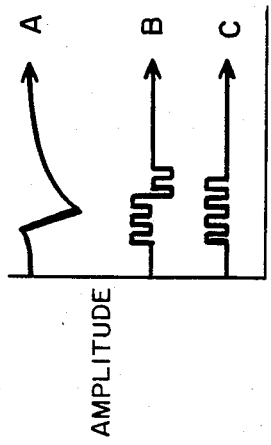
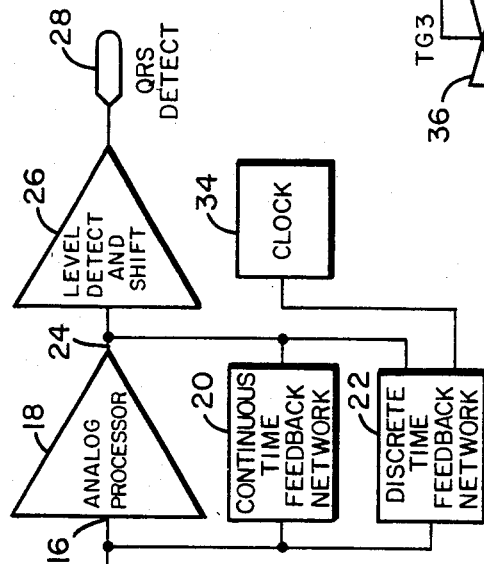
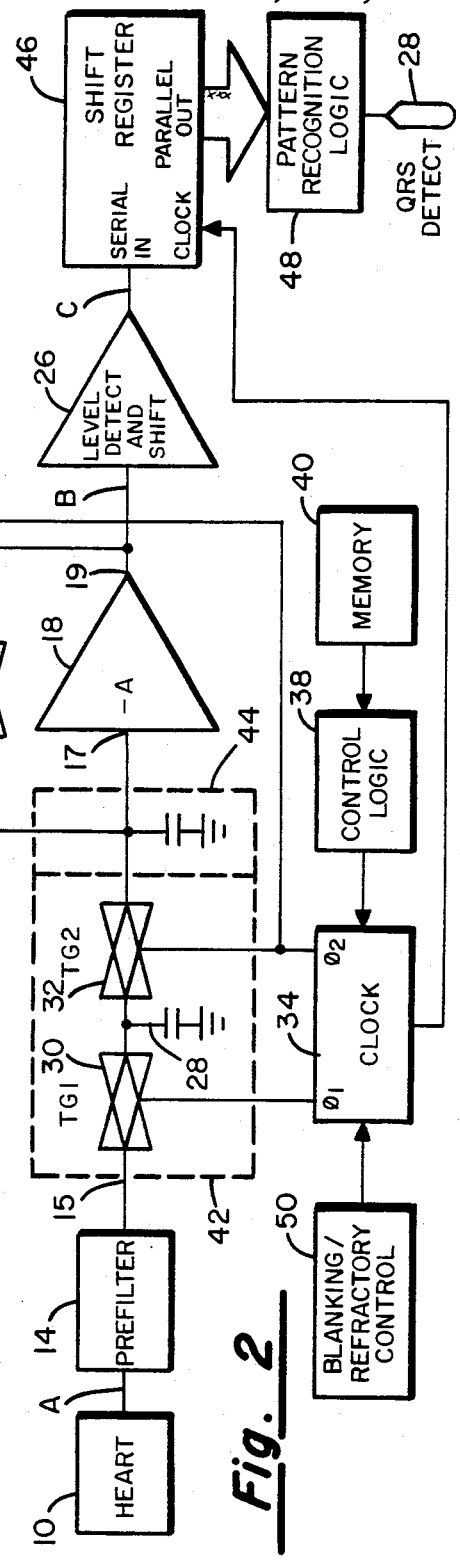

SAMPLED DATA SENSE AMPLIFIER

BACKGROUND OF THE INVENTION

1. Field of Invention

This invention relates to implantable medical devices and, more particularly, to a sense amplifier for detecting electrical signals associated with physiological events.

2. Description of the Prior Art

Implantable medical devices for the therapeutic stimulation of the heart are well known in the art from U.S. Pat. No. 3,478,746, issued to Wilson Greatbatch, which discloses a demand pacemaker. The demand pacemaker delivers electrical energy to the heart to initiate depolarization of cardiac tissue. This stimulating regime is used to treat heart block by providing electrical stimulation in the absence of naturally occurring, spontaneous cardiac depolarizations. This operational mode requires that intrinsic or naturally occurring cardiac depolarizations be detected and communicated to the logic associated with the demand pacemaker. In the prior art, the portion of the pacer devoted to the detection of physiological signals is referred to as the sense amplifier; and modern examples of such sense, amplifier topologies can be found in U.S. Pat. No. 4,275,737 to David L. Thompson, et al.

This prior art patent application is representative of a continuous time bipolar circuit topology used for a modern low current pacemaker. The amplifier is integrated in bipolar technology in hybrid form with discrete resistor and capacitor components forming the feedback and filtering functions of the sense amplifier.

Although this form of sense amplifier construction has proved suitable for low-power devices, it requires different implementation technology from the digital portions of the pacemaker; and it further requires a relatively large number of discrete resistor and capacitor components which must be accomodated on the hybrid substrate, which increases the size and power consumption of the sense amplifier circuitry while reducing its reliability.

In contrast, the sense amplifier of the present invention relies on switched capacitor realization of resistor components and linear metal oxide semiconductor amplifier components to form the sense amplifier topology. The advantage of this implementation is that it may be fully integrated with the digital portions of the pacemaker circuitry in a monolithic fashion, producing a one-chip pacer.

Additional features of this invention permit the realization of blanking and refractory circuit functions without materially increasing the complexity of the completed sense amplifier.

SUMMARY OF THE INVENTION

In contrast to the prior art, the sampled data sense amplifier of the present invention includes a discrete time network which periodically samples and transfers input signal information as discrete units of charge.

In the simplest form, the discrete time network is used to simulate the resistor and capacitor feedback paths controlling an operational amplifier. In the preferred embodiment, the discrete time network operates in conjunction with an analog gain cell to provide a switched capacitor comparator for forming the derivative of an input waveform.

One feature of the switched capacitor comparator embodiment is that periodic noise at the sampling frequency produces no output of the sense amplifier, thus providing a high degree of noise immunity at the sampling frequency. This feature is exploited by providing a scanning clock circuitry for noise filtering.

BRIEF DESCRIPTION OF THE DRAWINGS

FIG. 1 is a schematic representation of the sampled analog sense amplifier of the present invention; and FIG. 2 is a schematic diagram showing the preferred embodiment of the sampled data sense amplifier; and FIG. 3 is a waveform tracing illustrating the voltage-time waveforms at various portions of the circuit of the preferred embodiment.

DETAILED DESCRIPTION OF THE PREFERRED EMBODIMENT

An understanding of the operation of the present invention is facilitated by a brief discussion of the nature of a typical physiological signal which is sensed by sense amplifiers.

The typical physiological waveform is generated by a depolarization wave passing the electrode used to couple the organ to the sense amplifier. In the case of the heart, the physiological electrogram is characterized by a relatively steep intrinsic deflection followed by a gradual reduction of the voltage to the isoelectric line. An example of an intracardiac R-wave is shown as waveform A in FIG. 3. When viewed in the frequency domain, the bulk of the energy of the wave is concentrated at low frequencies. Since intrinsic cardiac waveforms differ between patients and do not repeat identically even in the case of a single patient, the typical sense amplifier is implemented as a passband amplifier having gradual cutoff frequencies. The lack of sharp skirts in the filter response means that the sense amplifier may respond to or detect continuous wave interference at the normal power line frequencies of 50 or 60 Hertz.

An additional requirement of sense amplifiers for cardiac pacer application is a timed refractory period following a stimulated event. Typically, after a stimulating pulse has been delivered to the cardiac tissue, there exists a polarization potential between the electrode and the heart which may be mistaken for a cardiac depolarization by the sense amplifier which would inhibit the operation of the demand pacemaker. To avoid this, additional circuitry is provided in the sense amplifier to render it refractory or insensitive to inputs for a fixed time period after the delivery of a stimulating pulse. A typical refractory time period would be on the order of 200 milliseconds.

Turning now to FIG. 1, there is shown the most general form of the invention wherein the physiological signal generated by the heart 10 is passed through a prefilter 14 to the input 16 of an analog processing device 18. After processing by an analog processor implementing a transfer function determined by the feedback networks 20 and 22, the output is buffered through the level detect and level shift device 26 and is provided as a logic level output at lead 28.

The prefilter 14 addresses a problem common to all sample data systems. This problem is the possibility of high-frequency noise being aliased or folded into the passband of the sense amplifier by the sampling process. It is customary to provide an analog continuous time prefilter to eliminate such high-frequency noise from sampled analog systems. In the present invention, it is contemplated that the Hemholtz capacitance associated with the electrode, heart interface and the resistance of the intracardiac lead will result in an effective prefilter without the requirement of additional discrete components positioned on the hybrid substrate itself. However, in the event that high-amplitude, high-frequency noise is present in the environment in which the sense amplifier will be used, it may be desirable to provide a continuous time prefilter prior to the sampling system.

The analog processor 18 may be an operational amplifier. The transfer function of such an amplifier is determined by the feedback networks coupling the input and output of the device. As shown in FIG. 1, a continuous time feedback network 20 is shown in addition to a discrete time or sampling feedback network 22.

The two feedback paths 20 and 22 and the analog processor 18 may be configured to form a passband amplifier mimicking the transfer characteristic of a traditional sense amplifier as typified by the cited prior art. Suitable buffering circuitry 26 may be provided to buffer the output 24 of the analog processor 18 and provide a logic level interface for the QRS detect signal available at lead 28.

In FIG. 2, one particular embodiment of a sample data sense amplifier is shown. In this embodiment, the signal from the heart 10 is coupled to the prefilter through a lead system and is provided to the input 15 of the sampling circuit 42. The sampling circuitry consists of a pair of transmission gates 30 and 32 which are driven by non-overlapping clock pulses from clock 34. In operation, the voltage available at input 15 is periodically sampled and stored on sampling capacitor 28. During a subsequent portion of the sampling cycle, the charge on sampling capacitor 28 is transferred to the reference or storage capacitor 44. During the first part of the sampling process, the inverting gain cell 18 is initialized through transmission gate 36 which connects the input and output of the gain cell 18, forcing its output to one-half the supply voltage. During the subsequent portion of the sampling cycle, the transmission gate 32 is closed, which permits charge distribution to take place between the storage capacitor 44 and the input sampling capacitor 28. In operation, charge will either flow from 28 to 44 or vice versa, causing a corresponding increase or drop in the voltage level applied to the inverting gain cell input 17. The charge redistribution during the second portion of the sampling period is amplified by the gain cell and produces an amplified output at output 19.

In this fashion, the gain cell 18 is operating as a comparator, comparing sequential charge samples which represent the voltage of the input waveform at discrete time intervals. The comparator produces a logic level output indicating the direction of change between successive samples. After appropriate level detection and level shifting, the buffered output from buffer 26 is supplied to a serial-in-parallel-out shift register 46.

FIG. 3 shows the operational waveforms of the circuitry during operation. The input waveform delivered by the heart to the prefilter is shown in wavetrace A and may be found at point A in the circuitry of FIG. 3.

After sampling the input waveform and determining the direction of change of the input waveform, waveform B is produced at point B in FIG. 3. In this waveform the positive-going transitions indicate a negative-going input waveform and vice versa. After appropriate level detection and shifting in level detector 26, the buffered signal at point C in FIG. 3 is a pulse train having a number of pulses equal to the duration of the physiological waveform.

The serial input clocked in at the sampling frequency is a digital pulse train representing the duration and shape of the physiological signal. The parallel output of the shift register is presented to pattern recognition logic 48 which determines whether the features extracted from the physiological waveform meet the detection criteria for producing a QRS detect signal at lead 28.

It should be clear that other forms of pattern recognition detection can be used and that the shift register can be replaced by a counter which produces an overflow output if the input physiological waveform meets a required duration.

As previously mentioned, sense amplifiers are typically provided with blanking and refractory circuitry to render the circuit unresponsive to a waveform present at its input for a time period extending from a paced or stimulated event.

In the preferred embodiment, blanking or refractory may be accomplished by blanking and refractory control logic 50 which operates through clock 34 to keep transmission gate 30 open during the desired refractory time. By keeping transmission gate 30 open, the input signal is prevented from altering the charge on capacitor 28. During the refractory time, it is also desirable to open transmission gate 36 thus decreasing the amount of current drawn by the inverting gain cell 18.

Additional control logic 38 and associated memory 40 may be provided for noise immunity protection.

The broad passband response of sense amplifiers makes them susceptible to interference at power means frequencies. One of the principal characteristics of this form of interference is that it is periodic and, if sampled at its fundamental frequency, the discrete time sample will be identical since the same portion of the noise waveform is sampled at each time interval. In the preferred embodiment, the transfer function of the gain cell is that of a differentiator and, since the discrete time samples do not vary, the output of the inverting gain cell does not change. This feature may be used to scan for noise which is periodic in nature. If the output of the pattern recognition logic indicates that the sense amplifier is responding to an input signal with a duration much longer than a normal physiological waveform, then the control logic 38 will alter the clock frequency 34 in an effort to sample at a rate which is equal to the repetitive noise. In this fashion, the sense amplifier system will search for a sampling frequency which permits the detection of the physiological signal in the presence of continuous wave noise.

Having thus described the invention, I claim:

1. A sampled data sense amplifier for producing a QRS detect signal in response to R-wave signals generated by the heart comprising:
    an analog processor having an input and an output;
    coupling means for coupling R-waves to said input;
    a first continuous time feedback network connected between said input and said output;
    a second discrete time feedback network connected between said input and said output; and,
    a level detector coupled to said output for generating a QRS detect signal when an R-wave exceeds a predetermined level.

2. The device of claim 1 further comprising a continuous time prefilter for low pass filtering of said R-wave signals coupled between said R-wave coupling means and said input to said analog processor.

* * * * *